US00PP21412P3

(12) United States Plant Patent

Maslin et al.

(10) Patent No.: US PP21,412 P3

(45) Date of Patent: Oct. 26, 2010

(54) APPLE TREE NAMED 'PLMAS98'

(50) Latin Name: *Malus domestica*
Varietal Denomination: PLMAS98

(76) Inventors: Gordon Maslin, Seven Day Road, Manjimup, Western Australia (AU); Christina Maslin, Seven Day Road, Manjimup, Western Australia (AU)

( * ) Notice: Subject to any disclaimer, the term of this patent is extended or adjusted under 35 U.S.C. 154(b) by 11 days.

(21) Appl. No.: 12/082,245

(22) Filed: Apr. 8, 2008

(65) Prior Publication Data

US 2008/0263732 P1 Oct. 23, 2008

Related U.S. Application Data

(60) Provisional application No. 60/926,030, filed on Apr. 23, 2007.

(51) Int. Cl.
*A01H 5/00* (2006.01)

(52) U.S. Cl. ..... Plt./161

(58) Field of Classification Search ..... Plt./161
See application file for complete search history.

*Primary Examiner*—Susan B McCormick Ewoldt
(74) *Attorney, Agent, or Firm*—C. A. Whealy

(57) ABSTRACT

'PLMAS98' is a new apple tree that originated as a limb sport mutation of 'Cripps Pink' (U.S. Plant Pat. No. 7,880). The new variety is notable for its early maturity. Fruit of the new variety is mature and ready for harvest at least 15 days earlier than fruit of 'Cripps Pink.'

3 Drawing Sheets

Latin name of the genus and species of the plant claimed: *Malus domestica.*

Variety denomination: 'PLMAS98'.

BACKGROUND AND SUMMARY OF THE VARIETY

'PLMAS98' originated as a limb sport mutation of 'Cripps Pink' (U.S. Plant Pat. No. 7,880). It was discovered by the inventor in April 1999 in a cultivated orchard at Manjimup, Western Australia. 'PLMAS98' was asexually propagated in July 2000 by budding to 'M7A' (not patented) rootstock at Manjimup, and has been shown to remain true to type over successive generations.

'PLMAS98' is a new and distinct apple tree notable for its early maturity. Fruit of the new variety is mature and ready for harvest at least 15 days earlier than fruit of 'Cripps Pink.'

'PLMAS98' can be compared to 'Golden Delicious' (not patented). Fruits of 'PLMAS98' are denser, firmer and have higher acidity than fruits of 'Golden Delicious'. In addition, fruit skin color of 'PLMAS98' is pink in color whereas fruit skin color of 'Golden Delicious' is yellowish green in color.

BRIEF DESCRIPTION OF THE PHOTOGRAPHS

Figure 1:
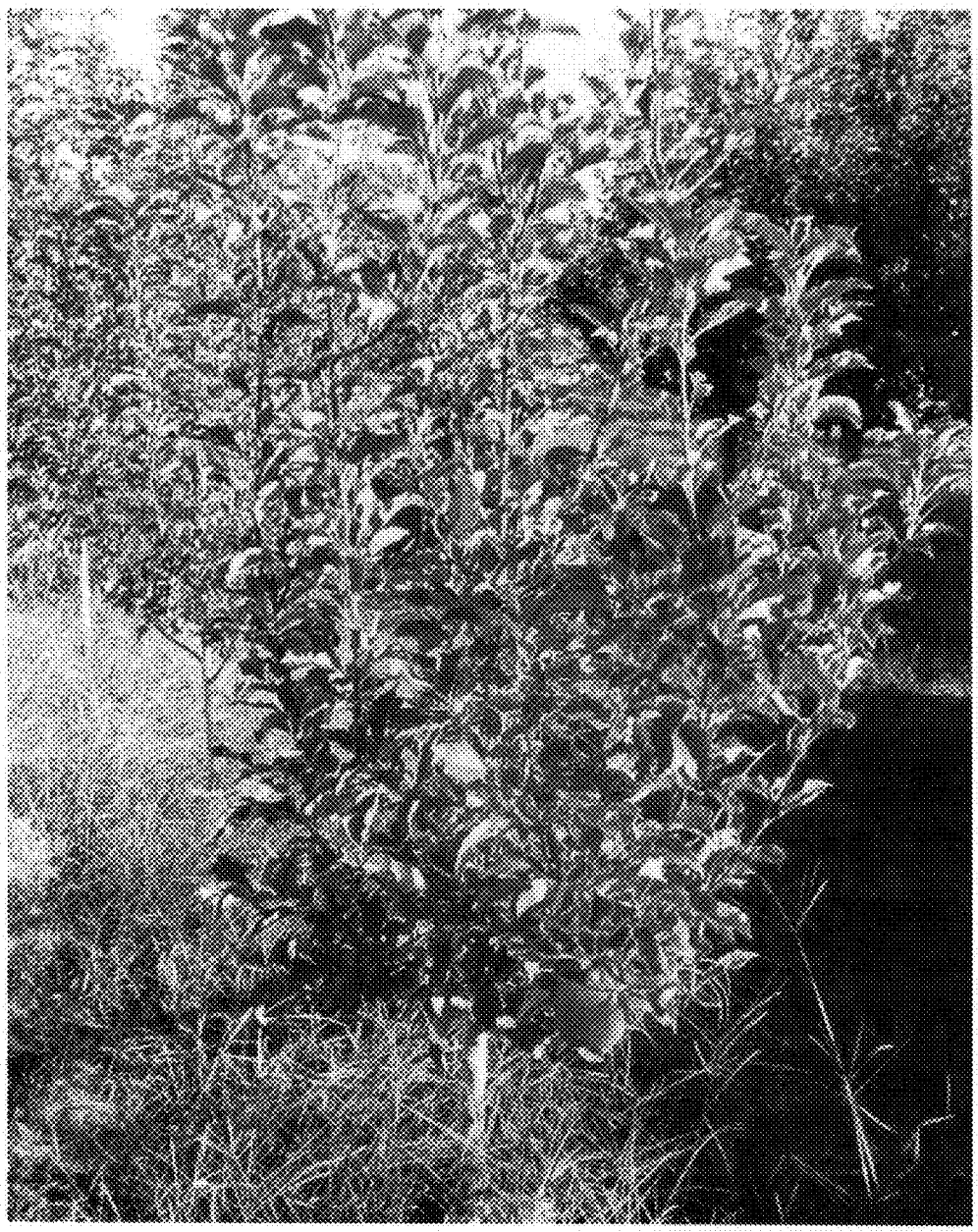
Figure 2:
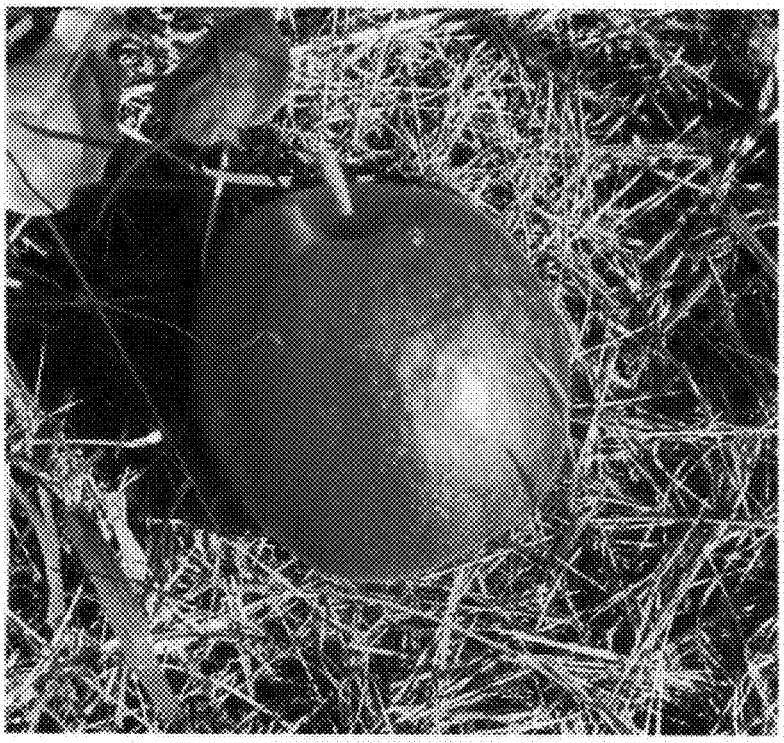
Figure 3:
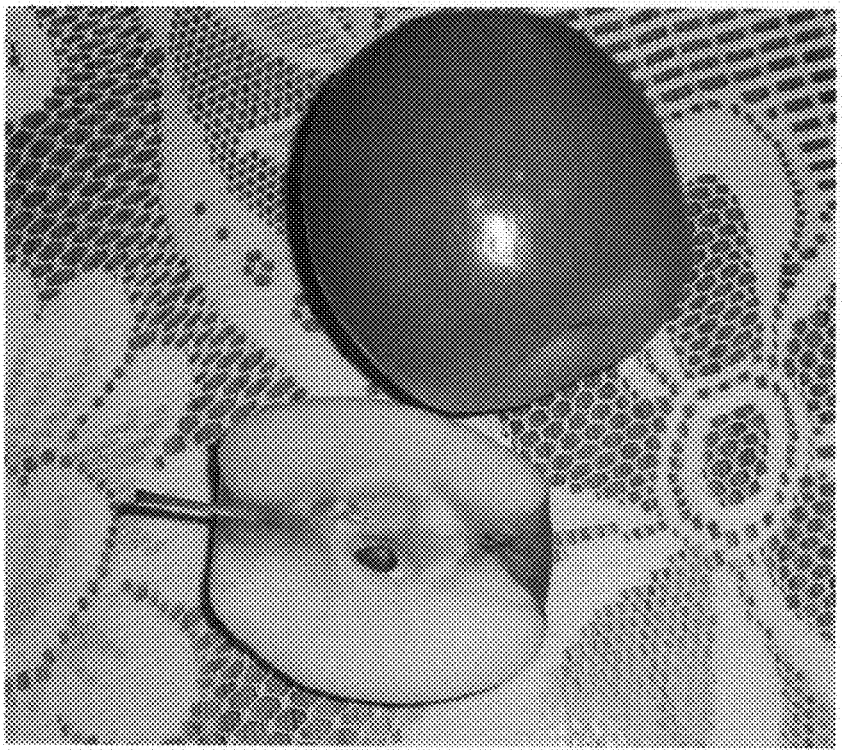

FIG. 1 shows the tree and fruit of the new variety;
FIG. 2 shows the fruit of the new variety; and
FIG. 3 shows the fruit of the new variety.

DETAILED BOTANICAL DESCRIPTION OF THE VARIETY

The following detailed botanical description is based on observations made during the 2007 growing season at Parker, Wash. on trees planted in 2003. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree
   - *Vigor.*—Vigorous.
   - *Type.*—Non-spur.
   - *Habit.*—Semi-erect.
   - *Size.*—Height 1.9 m; diameter 1.1 m.
   - *Trunk.*—Bark texture rough; Bark color—under color greyed-orange 165A, over color grey 201C, new growth greyed-orange 175A.
   - *Trunk diameter.*—At 12 mm above the soil level and above rootstock and bud, 22 mm.
   - *Branches.*—Length 47 cm; diameter 1 cm at base, 0.4 cm at tip; crotch angle 60° (measurements taken on secondary branch); color—under color greyed-orange 165A, over color grey 201C, new growth greyed-orange 175A.
   - *Winter hardiness.*—Hardy in area tested.
   - *Drought hardiness.*—Hardy in area tested.
   - *Temperature tolerance.*—Tolerant in area tested.
2. Dormant one year old shoot:
   - *Pubescence.*—Present.
   - *Size.*—Diameter 0.6 cm, length 35 cm.
   - *Color.*—Grey-brown 199A.
   - *Internode length.*—2 cm.
   - *Lenticels.*—Color yellow-white 158D; size 0.1 cm; quantity 8 to 10 per square inch.
3. Flowers:
   - *Ploidy level.*—Diploid; not self-fertile.
   - *Pollinators.*—Any other diploid.
   - *Bud.*—Quantity per spur 5; shape round; length 1 cm; diameter 0.9 cm; Color—outside red-purple 58C, tip white N155C.
   - *Flower.*—Diameter 4 cm; depth 1.5 cm; Quantity per cluster 5.
   - *Petals.*—Quantity per flower 5; overlapping; length 1.5 cm; width 1.5 cm; margin ruffled; color—edge red purple 58D, center white N155D.

*Sepals.*—Quantity per flower 5; shape pointed; length 0.5 cm, width 0.4 cm; color yellow-green 145B.
*Pedicel.*—Length 3.5 cm; diameter 0.1 cm; color yellow-green 146D.
*Stigma.*—Length 0.1 cm; color yellow 1C.
*Style.*—Length 0.9 cm; color yellow 1D.
*Ovary.*—Size 0.5 cm; color yellow-green N144C.
*Anthers.*—Quantity per flower 15; length 0.2 cm; pollen color yellow 1C.
*Bloom period.*—First bloom April 7; full bloom April 16 (Parker, Wash.).

4. Leaf:
*Attitude in relation to shoot.*—Upright.

5. Leaf blade:
*Size.*—Length 9 cm; width 6 cm.
*Width-length ratio.*—2:3.
*Margin.*—Serrate.
*Shape.*—Oval.
*Color.*—Upper surface green 137A; lower surface green 137A.

6. Petiole: Length 3 cm; diameter 0.5 cm; color yellow-green 145D.

7. Fruit:
*Size.*—Mass 195 g; diameter 78; height 83.
*Ratio of height to width.*—1:1.
*General shape in profile.*—Globose to oblong.
*Position of maximum diameter.*—Middle.
*Depth of eye basin.*—1.5 cm.
*Width of eye basin.*—2.4 cm.
*Eye aperature.*—Closed.
*Stalk.*—Diameter 0.5 cm; length 2 cm; color greyed-orange 177B.
*Stalk cavity.*—Depth 1.7 cm, width 1.8 cm.
*Size of lenticels.*—0.1 cm.
*Ground color of skin.*—Yellow-green 150B, with yellow-green 145B at stem.
*Over color of skin.*—Red-purple N57B.
*Amount of over color.*—95%.
*Intensity of over color.*—Very intense.
*Pattern of over color.*—Solid.
*Flesh.*—Crisp; juicy; color yellow-white 158B.
*Seeds.*—Shape oval; color greyed-orange 177A; width 0.5 cm, length 1 cm.
*Yield.*—Moderately heavy.
*Use.*—Fresh, cooking, juicing.
*Resistance to known diseases.*—None noted.
*Storageability.*—Good to excellent, 4 months in common storage.

I claim:

1. A new and distinct apple tree substantially as described and illustrated herein.

* * * * *